(12) United States Patent
Bergman

(10) Patent No.: US 8,877,124 B2
(45) Date of Patent: Nov. 4, 2014

(54) APPARATUS, SYSTEM, AND METHOD FOR EVALUATING AND ADJUSTING THE EFFECTIVENESS OF ULTRAVIOLET LIGHT DISINFECTION OF AREAS

(71) Applicant: Robert Bergman, Columbus, IN (US)

(72) Inventor: Robert Bergman, Columbus, IN (US)

( * ) Notice: Subject to any disclaimer, the term of this patent is extended or adjusted under 35 U.S.C. 154(b) by 0 days.

(21) Appl. No.: 14/167,085

(22) Filed: Jan. 29, 2014

(65) Prior Publication Data

US 2014/0212332 A1  Jul. 31, 2014

Related U.S. Application Data

(60) Provisional application No. 61/759,257, filed on Jan. 31, 2013.

(51) Int. Cl.
*A61L 2/10* (2006.01)
(52) U.S. Cl.
CPC ........................................ *A61L 2/10* (2013.01)
USPC ........................................................... 422/24
(58) Field of Classification Search
CPC ........................................................ A61L 2/10
USPC ................................ 422/24; 250/493.1, 504 R
See application file for complete search history.

(56) References Cited

U.S. PATENT DOCUMENTS

| | | |
|---|---|---|
| 2,215,635 A | 6/1939 | Collins |
| 3,691,140 A | 9/1972 | Silver |
| 4,684,685 A | 8/1987 | Shuman et al. |
| 4,786,812 A | 11/1988 | Humphreys |
| 4,952,369 A | 8/1990 | Belilos |
| 5,029,252 A | 7/1991 | Ameseder |
| 5,389,438 A | 2/1995 | Miller et al. |
| 5,446,289 A | 8/1995 | Shodeen et al. |
| 5,920,075 A | 7/1999 | Whitehead |
| 6,485,979 B1 | 11/2002 | Kippenhan et al. |
| 6,656,424 B1 | 12/2003 | Deal |
| 6,911,177 B2 | 6/2005 | Deal |
| 8,114,342 B2 | 2/2012 | Jung et al. |
| 8,178,042 B2 | 5/2012 | Jung et al. |
| 2002/0085947 A1* | 7/2002 | Deal ............................... 422/24 |
| 2012/0282135 A1* | 11/2012 | Trapani ............................ 422/3 |
| 2013/0168404 A1 | 7/2013 | Jour |

OTHER PUBLICATIONS

Derwent abstract 2008-N41742 for patent KR 796520 B1, published Jan. 2008; inventor: Jeong et al.*

* cited by examiner

*Primary Examiner* — Sean E Conley
(74) *Attorney, Agent, or Firm* — Roberts IP Law; John Roberts

(57) ABSTRACT

Provided is an apparatus, system, and method for evaluating and adjusting the effectiveness of ultraviolet light disinfection of areas such as hospital rooms or other areas. Provided in certain example embodiments are UV dosimeters adapted to visually indicate when they have been exposed to light in the UV C band range at a predetermined fluence level, the UV dosimeters being removably adhesable to surfaces in the room or area. Provided is an inexpensive, easy-to-use UV dosimeter and accompanying iterative process for optimizing UV disinfection parameters for a given area, including light source location(s), duration, and power level, and then recording that information for future use in connection with that area.

20 Claims, 5 Drawing Sheets

APPARATUS, SYSTEM, AND METHOD FOR EVALUATING AND ADJUSTING THE EFFECTIVENESS OF ULTRAVIOLET LIGHT DISINFECTION OF AREAS

CROSS-REFERENCE TO RELATED APPLICATIONS

The present application claims priority to and incorporates herein by reference U.S. Provisional Patent Application No. 61/759,257 to Bergman, entitled Apparatus, System, And Method For Evaluating And Adjusting The Effectiveness Of Ultraviolet Light Disinfection Of Areas, filed Jan. 31, 2013.

FEDERALLY SPONSORED RESEARCH OR DEVELOPMENT

None.

TECHNICAL FIELD

The present invention relates generally to an apparatus, system, and method for evaluating and adjusting the effectiveness of ultraviolet light disinfection of areas, such as, for example, rooms in hospitals and clinics and clean rooms associated with manufacturing or testing.

BACKGROUND

Surface disinfection of patient care areas is a key factor in the constant battle to reduce or eliminate Hospital Acquired Infections (HAIs), also known in the art as nosocomial diseases or infections. Increased evidence published in scientific literature confirms that *Clostridium difficile*, MRSA, VRE, *Acinetobacter baumannii, Bacillus subtilis* var. *niger, Bacillus anthracis* Sterne, and influenza are transmitted via environmental surfaces and air. The problem has become so serious that many hospitals must close critical areas, such as operation theaters and intensive care units, to eradicate pathogens via terminal cleaning. HAIs contribute to rising health care costs and can lead to severe, if not lethal, effects on patients.

Surface disinfection of patient care areas can be performed by exposing surfaces to a dose (also referred to herein as "fluence") of UV-C light, which is a form of electromagnetic intensity that is harmful to micro-organisms such as pathogens, viruses, and molds. Fluence is a measure of the quantity of light or other intensity impinging from all directions on the smallest possible three dimensional object. Fluence is often expressed in millijoules per square centimeter ($mJ/cm^2$).

Ultraviolet germicidal irintensity (UVGI) is a sterilization method that uses ultraviolet (UV) intensity at a sufficiently short wavelength to break down micro-organisms. The short wavelength of UV-C is harmful to forms of life at the microorganic level by destroying nucleic acids in these organisms so that their DNA and/or RNA chemical structure is disrupted by the UV intensity. The disruption prevents micro-organisms from replicating, thereby rendering them inactive and unable to cause infection. The primary mechanism of inactivation by UV is the creation of pyrimidine dimers, which are bonds formed between adjacent pairs of thymine or cytosine pyrimidines on the same DNA or RNA strand.

Low-pressure mercury lamps may be used for disinfection applications because they emit two narrow peak wavelengths of light at 185 nm and 254 nm, the latter peak being close to the wavelength where DNA and RNA experience maximum UV absorption (253.7 nm). The 185 nm emission causes disassociation of oxygen molecules to create ozone, a gas with a short half-life that is an air pollutant with harmful effects on respiratory systems. The EPA has designated a safe concentration of ozone concentration to be 0.05 ppm in air. Therefore, UV lamps that generate ozone are generally undesirable for use in closed areas.

A primary benefit of using UV light for disinfection is that it does not contain or create any residuals or byproducts, such as can occur with chemical methods of purification. In fact, UV light is sometimes used to remove residuals, and disinfection by-products, such as chlorine, peroxide, ozone, and trihalomethanes, that can result from other purification processes.

Different species of microorganisms require varying levels of UV-C exposure, but nearly all can be effectively inactivated with a fluence level of about 30 $mJ/cm^2$ of surface area. Fluence levels of this intensity can achieve a 4-log reduction for most microorganisms, equivalent to a 99.99% reduction in the number of active organisms.

However, the effectiveness of UV surface disinfection is dependent on line-of-sight exposure of the micro-organisms to the UV source. Environments with obstacles that block the source are not as effective, and UV reflectance may be low and unreliable. In such an environment, such as a typical hospital room, effectiveness is then reliant on the placement of the source system so that line-of-sight is optimum for surface disinfection. The effectiveness of a surface disinfection unit (SDU) in such an environment depends on a number of factors, including the length of time a micro-organism is exposed to UV; power fluctuations of the UV source that impact the wavelength; the distance of the surface from the intensity source; the ambient temperature; the humidity of the air; the presence of particles in the air; the presence of dust and dirt on the lamp surface; the presence of particles that can protect the micro-organisms from UV; and a microorganism's ability to withstand UV during its exposure.

Various efforts have been made to improve line-of-sight exposure of the micro-organisms to the UV source. For example, a portable room disinfection unit employing a plurality of UV lamps on a single base unit has reportedly been available under the trade name TRU-D from Lumalier Corporation, Memphis, Tenn., USA. The tubular lamps are disposed vertically about a vertical axis and irradiate radially in different directions. A shortcoming of such a single-unit ultraviolet area sterilizer (UVAS) is that any equipment or appurtenances in the room, such as beds, tables, and chairs must necessarily create shadow areas which can be irradiated only at a reduced intensity by reflections.

U.S. Pat. Nos. 6,656,424 and 6,911,177 are both incorporated herein by reference in their entireties, and disclose a method and apparatus for a mobile or stationary automated UVAS. The UVAS is positioned in a room, such as an operating room or intensive care unit, where concern exists regarding the presence of pathogenic bacteria on environmental surfaces. For an initial interval after actuation, motion detectors sense movement, to assure that personnel have evacuated the space to be sterilized. Subsequently, UV-C generators, such as a bank of mercury bulbs, generate intense levels of UV-C. After the bulbs have reached a steady state of output, an array of UV-C sensors scan the room to determine the darkest area, or the area reflecting the lowest level of UV-C back to the sensors. A basic stamp contained in the device calculates the time required to obtain a bactericidal dose of UV-C reflected back from darkest area. The UVAS transmits the calculated dose of UV-C, as well as other monitoring information, to the remote control where it is displayed to the user. Once a bactericidal dose has been reflected to all the sensors, the unit notifies the user and shuts down. By relying on reflected doses rather than direct exposure, the UVAS purportedly is able to sterilize or sanitize all surfaces within the room that are within view of an exposed wall or ceiling.

As noted above for the TRU-D UVAS, a shortcoming of such a single-unit UVAS is that any equipment or appurtenances in the room, such as beds, tables, and chairs must necessarily create shadow areas which can be irradiated only at a reduced intensity by reflections. Further, auxiliary spaces, such a bathroom that commonly accompanies a hospital room, cannot be properly irradiated by a single UVAS, so a second UVAS is required. The patent references disclose an embodiment wherein a second UV lamp may be disposed apart from the UVAS, but powered and controlled by the UVAS, to assist in irradiating shadow areas of the UVAS. U.S. patent publication number US20120305787 A1 to Henson, application Ser. No. 13/153,408, published Dec. 6, 2012, is incorporated herein by reference in its entirety and discloses a UV surface disinfection system comprising a plurality of independently placeable and independently controllable surface disinfection units controlled by a single remote control console, each unit having a single ultraviolet lamp.

These real and proposed UV disinfection systems are employing increasingly complicated and expensive means to improve line-of-sight exposure of the micro-organisms to the UV source. In use, however, even the most advanced systems still require a user to largely guess whether they have placed the UVAS device(s) in the right location(s), and whether they have used them long enough at high enough power levels to sufficiently disinfect all the surfaces in a room, including hard-to-clean, shadowed and often overlooked high-touch surfaces such as electronic keyboards, remotes, and computers. What is needed is an inexpensive, easy-to-use apparatus, system, and method for evaluating the effectiveness of a given ultraviolet light disinfection of a room, which allows adjustments to be made to the location(s) and other parameters of the UV lamp(s) until the optimal treatment parameters for a given room can be established.

SUMMARY

The present invention elegantly addresses all the above challenges and provides numerous additional benefits. In various example embodiments the solution discovered by the present inventor may comprise providing a plurality of relatively-inexpensive, disposable, removably-adherable UV dosimeters, and a system and method of using the same, comprising, for example, removably adhering a plurality of the UV dosimeters distally around an area to be disinfected by UV light, applying UV light to the area in a wavelength and dosage appropriate for sterilizing similar areas, for instance with one or more ultraviolet area sterilizers (UVAS), and then evaluating the UV dosimeters to determine which ones received a sufficient sterilizing dosage of UV light. If any of the UV dosimeters indicate that an insufficient dosage of UV light was received, it is then indicated that more UV light needs to be directed to the area where that or those UV dosimeter(s) were located. Changes can then be made to the location(s) of the UVAS devices, and/or their power levels or the duration of their use, and the above steps repeated until a satisfactory result is obtained at all UV dosimeter locations. Once a satisfactory result is obtained for all identified surfaces, the parameters of that UV treatment, including location(s) of UVAS device(s), duration of use, power level, etc., can be recorded so that subsequent UV sterilizations for a particular area can be carried out in an identical manner in the future, thereby providing assurance that subsequent UV sterilizations will sufficiently treat all areas of the room.

For example, provided in certain example embodiments is a method of sterilizing an area, comprising the steps of: removably adhering two or more UV dosimeters to surfaces in a plurality of locations in an area to be sterilized, the two or more UV dosimeters adapted to visually indicate when the respective two or more UV dosimeters have been exposed to light in the UV C band range at a predetermined a fluence level, the two or more UV dosimeters being removably adhesable to each other and to surfaces in the area to be sterilized; positioning one or more UV sterilizers in one or more first respective locations in the area to be sterilized, the one or more UV sterilizers comprising at least one source of ultraviolet light substantially in the UV C band range; evacuating personnel from the area to be sterilized; sterilizing at least a portion of the area by causing the one or more UV sterilizers to emit ultraviolet light substantially in the UV C band range in the area to be sterilized for a predetermined first time at a predetermined first power level; visually inspecting the two or more UV dosimeters and evaluating whether any of the two or more UV dosimeters do not indicate exposure to light in the UV C band range at the predetermined fluence level; when any of the two or more UV dosimeters do not indicate exposure to light in the UV C band range at the predetermined fluence level, repeating each of the above steps using fresh UV dosimeters that have not been exposed to light in the UV C band range, while modifying the sterilizing step by positioning the one or more UV sterilizers in one or more respective locations different than the one or more respective locations used in the preceding sterilizing steps; and repeating each of the above steps until all of the two or more UV dosimeters used in a given sterilizing step indicate exposure to light in the UV C band range at the predetermined fluence level.

Example methods may further comprising the steps of: documenting the one or more respective locations of the one or more UV sterilizers that caused all of the two or more UV dosimeters used in a given sterilizing step to indicate exposure to light in the UV C band range at the predetermined fluence level. Methods may further comprise the steps of: sterilizing the area by positioning the one or more UV sterilizers in locations based on documentation created during the documenting step.

Provided in certain example embodiments is a method of sterilizing an area comprising the steps of: removably adhering two or more UV dosimeters to surfaces in a plurality of locations in an area to be sterilized, the two or more UV dosimeters adapted to visually indicate when the respective two or more UV dosimeters have been exposed to light in the UV C band range at a predetermined a fluence level, the two or more UV dosimeters being removably adhesable to each other and to surfaces in the area to be sterilized; positioning one or more UV sterilizers in one or more first respective locations in the area to be sterilized, the one or more UV sterilizers comprising at least one source of ultraviolet light substantially in the UV C band range; evacuating personnel from the area to be sterilized; sterilizing at least a portion of the area by causing the one or more UV sterilizers to emit ultraviolet light substantially in the UV C band range in the area to be sterilized for a predetermined first time at a predetermined first power level; visually inspecting the two or more UV dosimeters and evaluating whether any of the two or more UV dosimeters do not indicate exposure to light in the UV C band range at the predetermined fluence level; when any of the two or more UV dosimeters do not indicate exposure to light in the UV C band range at the predetermined fluence level, repeating each of the above steps using fresh UV dosimeters that have not been exposed to light in the UV C band range, while modifying the sterilizing step by causing the one or more UV sterilizers to emit ultraviolet light substantially in the UV C band range in the area to be sterilized for a time longer than the time in the immediately preceding sterilizing step; and repeating each of the above steps until all of the two or more UV dosimeters used in a given sterilizing step indicate exposure to light in the UV C band range at the predetermined fluence level.

Example methods may further comprise the steps of: documenting the length of time that the one or more UV sterilizers emitted ultraviolet light substantially in the UV C band range that caused all of the two or more UV dosimeters used in a given sterilizing step to indicate exposure to light in the UV C band range at the predetermined fluence level. Methods may further comprise the steps of: sterilizing the area by causing the one or more UV sterilizers to emit ultraviolet light substantially in the UV C band range for a length of time determined based on documentation created during the documenting step.

Provided in certain example embodiments is a method of sterilizing an area comprising the steps of: removably adhering two or more UV dosimeters to surfaces in a plurality of locations in an area to be sterilized, the two or more UV dosimeters adapted to visually indicate when the respective two or more UV dosimeters have been exposed to light in the UV C band range at a predetermined a fluence level, the two or more UV dosimeters being removably adhesable to each other and to surfaces in the area to be sterilized; positioning one or more UV sterilizers in one or more first respective locations in the area to be sterilized, the one or more UV sterilizers comprising at least one source of ultraviolet light substantially in the UV C band range; evacuating personnel from the area to be sterilized; sterilizing at least a portion of the area by causing the one or more UV sterilizers to emit ultraviolet light substantially in the UV C band range in the area to be sterilized for a predetermined first time at a predetermined first power level; visually inspecting the two or more UV dosimeters and evaluating whether any of the two or more UV dosimeters do not indicate exposure to light in the UV C band range at the predetermined fluence level; when any of the two or more UV dosimeters do not indicate exposure to light in the UV C band range at the predetermined fluence level, repeating each of the above steps using fresh UV dosimeters that have not been exposed to light in the UV C band range, while modifying the sterilizing step by causing the one or more UV sterilizers to emit ultraviolet light substantially in the UV C band range in the area to be sterilized at a power level higher than the power level in the immediately preceding sterilizing step; and repeating each of the above steps until all of the two or more UV dosimeters used in a given sterilizing step indicate exposure to light in the UV C band range at the predetermined fluence level.

Example methods may further comprise the steps of: documenting the power level at which the one or more UV sterilizers emitted ultraviolet light substantially in the UV C band range that caused all of the two or more UV dosimeters used in a given sterilizing step to indicate exposure to light in the UV C band range at the predetermined fluence level. Methods may further comprise the steps of: sterilizing the area by causing the one or more UV sterilizers to emit ultraviolet light substantially in the UV C band range at a power level determined based on documentation created during the documenting step.

Example methods may further comprising the steps of: identifying and documenting the location of objects in the area when all of the two or more UV dosimeters used in a given sterilizing step indicate exposure to light in the UV C band range at the predetermined fluence level, where the objects are selected from the group consisting of: furniture, electronics, medical equipment.

In various embodiments the predetermined fluence level is at least 15 mJ/cm$^2$ of surface area, at least 20 mJ/cm$^2$ of surface area, or at least 40 mJ/cm$^2$ of surface area, or any levels there between or higher.

Further details regarding example embodiments of the invention are provided below with reference to the accompanying example figures. Additional aspects, alternatives and variations as would be apparent to persons of skill in the art are also disclosed herein and are specifically contemplated as included as part of the invention, which is limited not by any example but only by the claims.

BRIEF DESCRIPTION OF THE DRAWINGS

The accompanying figures incorporated by reference illustrate certain aspects of example embodiments of the invention. FIGS. 2 through 4B are not drawn to scale, but rather show certain aspects as enlarged for clarity.

FIG. 3 is a side elevation view of a stack of the example UV dosimeters of FIG. 2A, with thicknesses shown exaggerated for clarity, according to various example embodiments.

FIG. 4A is a top plan view of an example room or other space with a plurality of the example UV dosimeters of FIG. 2A applied to a plurality of distally located surfaces therein, with a UV light source located in a first position, according to various example embodiments.

FIG. 4B is a top plan view of the example room or other space of FIG. 4A, with the UV light source located in a second position, according to various example embodiments.

DETAILED DESCRIPTION OF EXAMPLE EMBODIMENTS

Reference is made herein to some specific examples of the present invention, including any best modes contemplated by the inventor for carrying out the invention. Examples of these specific embodiments are illustrated in the accompanying figures. While the invention is described in conjunction with these specific embodiments, it will be understood that it is not intended to limit the invention to the described or illustrated embodiments. To the contrary, it is intended to cover alternatives, modifications, and equivalents as may be included within the spirit and scope of the invention as defined by the appended claims. Example embodiments of the invention will now be described.

Example UV Dosimeters

Figure 1:
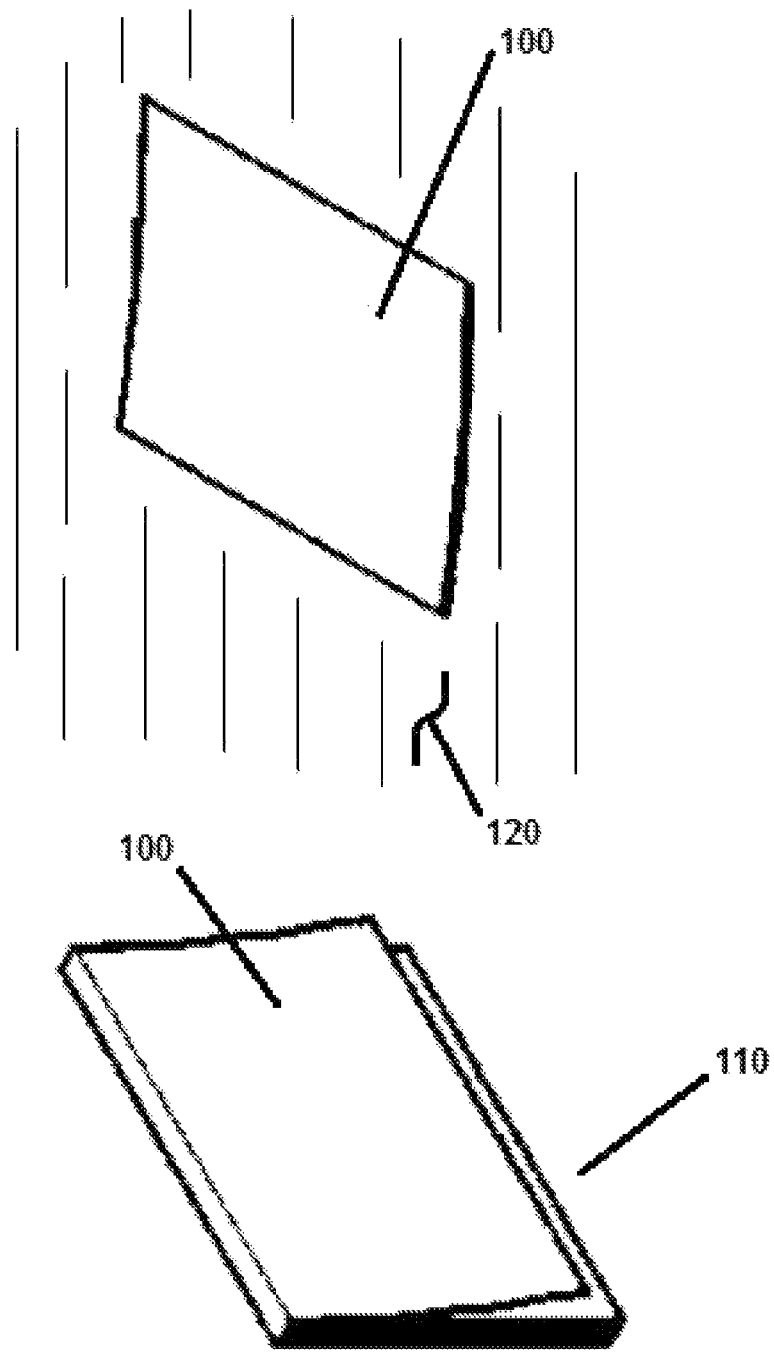
FIG. 1 provides a perspective view of prior art "sticky notes" in a stack and with one sheet removed from the stack and applied to a surface, as is known in the art.

Turning first to FIG. 1, Applicant is aware of "sticky notes" such as Post-it™ notes 110 manufactured by 3M of Minneapolis, Minn., which are well known for allowing releasable mounting of sheets of paper 100 to solid objects or surfaces 120. The Post-it™ notes 110 are typically used for making annotations which may be temporarily placed where it is convenient, and then removed without leaving residue from the chemical adhesives found on the back of an upper portion of each sheet 100. A further advantage of sticky notes such as Post-it™ notes 110 is that removal of the note 100 does not ordinarily damage the surface 120 to which the note 100 was mounted.

Applicant has devised a UV dosimeter 200, an example of which is shown in FIGS. 2A through 4B, which may be used in a similar fashion to Post-it™ or sticky notes 100 with the advantage that the UV dosimeters 200 can be inexpensively manufactured in stacks 210 or dispensers (see, e.g., US 20130168404 A1, Removable Notepaper Dispenser, incorporated herein by reference) like Post-it™ notes 110, such that a single UV dosimeter sheet 200 can be peeled off the stack 210 and/or removed from a dispenser (an example incorporated by reference above), and then removably adhered to any surface 120 in a room 450, like Post-it™ notes 100. Once the UV disinfecting testing is complete the UV dosimeters 200 can be easily removed from whatever surfaces 120 they are adhered to, without leaving residue on or otherwise damaging the surfaces 120 on which they were applied, once again, like Post-it™ notes 100. It may be advantageous to store the UV dosimeters 200 in a container that may or may not itself be a dispenser (an example incorporated by reference above), where the container substantially prevents UV intensity 410 from reaching the unused UV dosimeters 200. Alternatively, in certain embodiments the UV dosimeters 200 may be provided in an adhered stack 210 of sheets 200, like Post-it™ notes 110, where an uppermost sheet or covering 250 protects the underlying sheets 200 from UV intensity 410 (which may come from the sun, lights, etc., in addition to a UV-specific device 400).

Figure 2A:
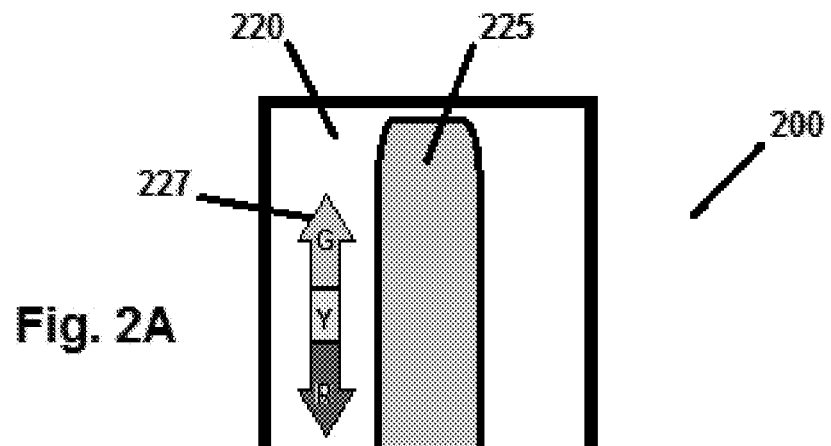
FIG. 2A is a top plan view of an example UV dosimeter according to one embodiment, according to various example embodiments.
Figure 2B:
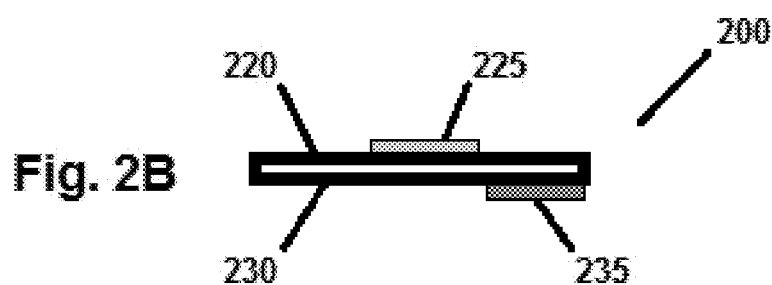
FIG. 2B is a side elevation view of the example UV dosimeter of FIG. 2A, with thicknesses shown exaggerated for clarity, according to various example embodiments.
Figure 2C:
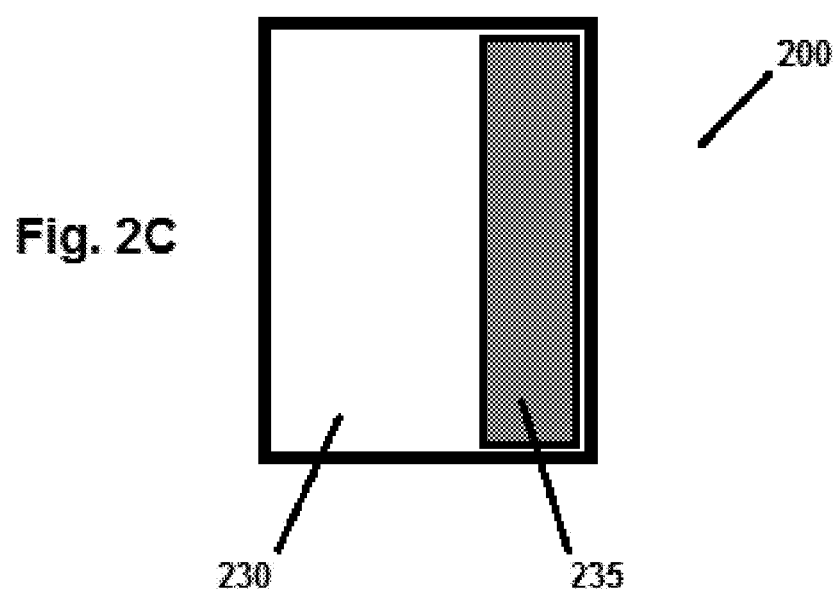
FIG. 2C is a bottom plan view of the example UV dosimeter of FIG. 2A, according to various example embodiments.
Figure 3:
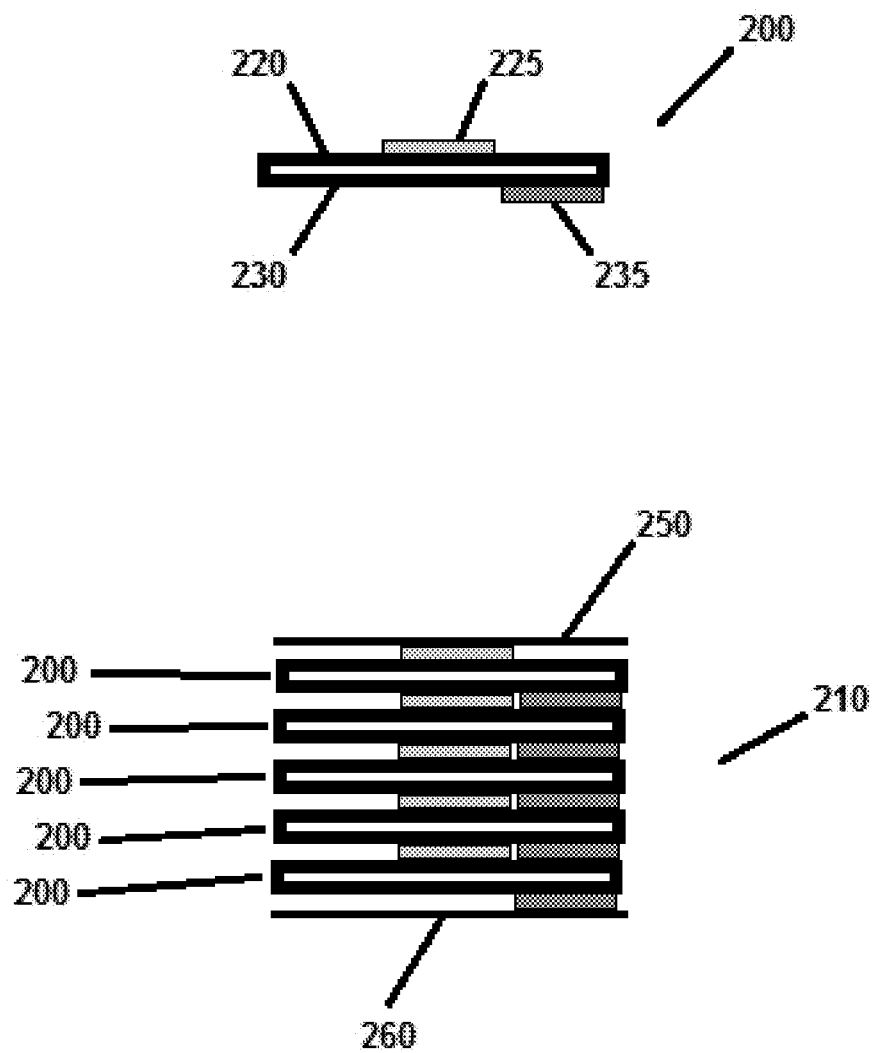

Example UV dosimeters 200 as shown in FIGS. 2A through 2C may be formed partially, primarily, or entirely from any suitable materials, such as paper or plastic or any combination thereof, and may be formed in any suitable shape (such as round, triangular, square, rectangular (shown), irregular, or any other suitable shape), and may comprise a top surface 220 comprising, bearing or displaying a color-changing or darkening composition or region 225 and a comparison chart 227, as well as a bottom surface 230 with at least one sticky region 235. The sticky region 235 may be the same or similar in size, shape, and chemical composition to the corresponding sticky surface on the bottom of conventional Post-it™ or "sticky notes" 100. Alternatively, any suitable treatment may be applied to sticky region 235 to make the UV dosimeters 200 removably adherable to typical surfaces 120 in a room 450 (such as walls, counters, floors, ceilings, furniture, fixtures, electronics, artwork, etc.) without damaging those surfaces 120. These attributes may be obtained for example through the use of tacky microspheres coated onto a paper substrate as disclosed in U.S. Pat. No. 3,691,140, which is incorporated herein by reference. Similarly-functioning removable adhesive technologies are disclosed in U.S. Pat. Nos. 4,684,685 and 5,389,438, both of which are incorporated herein by reference. Example UV dosimeters 200 may be paper-thin in practice, though shown in FIGS. 2A through 4B as having thickness for purposes of illustration (thickness meaning the distance from the top surface 220 to the bottom surface 230). Likewise, for purposes of illustration the sticky region 235 and color-changing or darkening composition or region 225 are shown as having visible thicknesses, while in practice these may be chemical layers that have no or negligible visible thicknesses.

As best shown in FIG. 2A, a photosensitive composition may be applied to, formed into, or appear in the color-changing or darkening region 225 of the UV dosimeters 200, which region 225 may be capable of offering a visual, calibrated, predetermined reaction to the presence of ultraviolet intensity 410. Various suitable photosensitive compositions for use in region 225 are known in the art, and the following U.S. patents are incorporated herein by reference: U.S. Pat. No. 3,202,821, U.S. Pat. No. 3,393,318, U.S. Pat. No. 3,773,511, U.S. Pat. No. 4,001,587, U.S. Pat. No. 4,130,760, U.S. Pat. No. 4,466,941, U.S. Pat. No. 4,507,226, U.S. Pat. No. 4,698,296, U.S. Pat. No. 4,705,741, U.S. Pat. No. 4,705,742, U.S. Pat. No. 4,734,355, U.S. Pat. No. 4,784,934, U.S. Pat. No. 4,788,126, U.S. Pat. No. 4,788,433, U.S. Pat. No. 4,918,317, U.S. Pat. No. 4,952,244, U.S. Pat. No. 4,954,428, U.S. Pat. No. 4,970,137, U.S. Pat. No. 5,002,852, U.S. Pat. No. 5,028,792, U.S. Pat. No. 5,051,597, U.S. Pat. No. 5,084,623, U.S. Pat. No. 5,137,964, U.S. Pat. No. 5,139,927, U.S. Pat. No. 5,139,928, U.S. Pat. No. 5,147,787, U.S. Pat. No. 5,149,617, U.S. Pat. No. 5,215,869, U.S. Pat. No. 5,215,870, U.S. Pat. No. 5,232,820, U.S. Pat. No. 5,296,275, U.S. Pat. No. 5,359,200, U.S. Pat. No. 5,378,896, U.S. Pat. No. 5,387,798, U.S. Pat. No. 5,411,835, U.S. Pat. No. 5,420,000, U.S. Pat. No. 5,436,115, U.S. Pat. No. 5,543,137, U.S. Pat. No. 5,562,896, U.S. Pat. No. 5,576,551, U.S. Pat. No. 5,581,090, U.S. Pat. No. 5,589,398, U.S. Pat. No. 5,616,443, U.S. Pat. No. 5,637,876, U.S. Pat. No. 5,643,356, U.S. Pat. No. 5,643,701, U.S. Pat. No. 5,645,964, U.S. Pat. No. 5,681,380, U.S. Pat. No. 5,683,843, U.S. Pat. No. 5,685,754, U.S. Pat. No. 5,686,503, U.S. Pat. No. 5,700,850, U.S. Pat. No. 5,709,955, U.S. Pat. No. 5,721,287, U.S. Pat. No. 5,732,112, U.S. Pat. No. 5,733,693, U.S. Pat. No. 5,739,175, U.S. Pat. No. 5,747,550, U.S. Pat. No. 5,767,520, U.S. Pat. No. 5,773,182, U.S. Pat. No. 5,777,341, U.S. Pat. No. 5,782,963, U.S. Pat. No. 5,783,110, U.S. Pat. No. 5,786,132, U.S. Pat. No. 5,798,015, U.S. Pat. No. 5,811,199, U.S. Pat. No. 5,837,429, U.S. Pat. No. 5,849,411, U.S. Pat. No. 5,855,655, U.S. Pat. No. 5,858,586, U.S. Pat. No. 5,865,471, U.S. Pat. No. 5,885,337, U.S. Pat. No. 5,891,229, U.S. Pat. No. 5,908,495, U.S. Pat. No. 5,914,197, U.S. Pat. No. 5,942,554, U.S. Pat. No. 5,951,909, U.S. Pat. No. 6,008,268, U.S. Pat. No. 6,015,621, U.S. Pat. No. 6,017,471, U.S. Pat. No. 6,017,661, U.S. Pat. No. 6,033,465, U.S. Pat. No. 6,046,455, U.S. Pat. No. 6,054,256, U.S. Pat. No. 6,060,200, U.S. Pat. No. 6,060,223, U.S. Pat. No. 6,063,551, U.S. Pat. No. 6,066,439, U.S. Pat. No. 6,071,979, U.S. Pat. No. 6,090,236, U.S. Pat. No. 6,099,628, U.S. Pat. No. 6,120,949, U.S. Pat. No. 6,127,073, U.S. Pat. No. 6,168,654, U.S. Pat. No. 6,168,655, U.S. Pat. No. 6,177,578, U.S. Pat. No. 6,198,108, U.S. Pat. No. 6,211,383, U.S. Pat. No. 6,228,157, U.S. Pat. No. 6,235,095, U.S. Pat. No. 6,242,057, U.S. Pat. No. 6,265,458, U.S. Pat. No. 6,268,602, U.S. Pat. No. 6,277,897, U.S. Pat. No. 6,285,031, U.S. Pat. No. 6,294,698, U.S. Pat. No. 6,294,792, U.S. Pat. No. 6,331,056, U.S. Pat. No. 6,342,305, U.S. Pat. No. 6,368,395, U.S. Pat. No. 6,368,396, U.S. Pat. No. 6,420,089, U.S. Pat. No. 6,433,035, U.S. Pat. No. 6,465,791, U.S. Pat. No. 6,470,891, U.S. Pat. No. 6,475,433, U.S. Pat. No. 6,486,227, U.S. Pat. No. 6,503,559, U.S. Pat. No. 6,504,161, U.S. Pat. No. 6,504,161, U.S. Pat. No. 6,524,379, U.S. Pat. No. 6,734,440, U.S. Pat. No. 7,147,801, U.S. Pat. No. 7,184,569, U.S. Pat. No. 7,220,535, U.S. Pat. No. 7,227,158, U.S. Pat. No. 7,304,317, U.S. Pat. No. 7,393,623, U.S. Pat. No. 7,399,977, U.S. Pat. No. 7,420,187, U.S. Pat. No. 7,476,874, U.S. Pat. No. 7,482,601, U.S. Pat. No. 7,518,126, U.S. Pat. No. 7,529,385, U.S. Pat. No. 7,531,095, U.S. Pat. No. 7,575,253, U.S. Pat. No. 7,589,331, U.S. Pat.

No. 8,097,668, U.S. Pat. No. 8,115,182, U.S. Pat. No. 8,133,735, U.S. Pat. No. 8,143,063, U.S. Pat. No. 8,242,464, U.S. Pat. No. D580,281.

For example, a composition for use in region 225 may comprise a complex of a leuco dye and animal-derived serum albumin. The preparation of this complex has reportedly been found to stabilize the leuco dyes, to avoid fading after the presentation of a color reaction upon exposure to UV intensity 410. Also, the leuco dye-serum albumin albumin complex is reportedly capable of exacting calibration, so that scientifically significant quantitative measurements of ultraviolet light exposure can be made. Using these and other technologies known in the art, it would be apparent to persons of skill in the art how to calibrate a UV dosimeter 200 to provide a visual indication 227 when the UV dosimeter 200 has been exposed to UV intensity 410 sufficient to sterilize an area 450. For example, UV dosimeters may be calibrated by exposing a UV dosimeter 200 of known chemical composition to a fluence level of UV intensity 410 of about 30 mJ/cm$^2$ of surface area, which is sufficient to achieve a 4-log reduction for most microorganisms, equivalent to a 99.99% reduction in the number of active organisms, noting the resultant color change of the UV dose indicating region 225 on the UV dosimeter 200, and documenting that color change on a calibrated color bar or chart 227, thereby indicating the standard to meet on subsequent UV dosimeters 200. The UV dosimeter 200 can also be calibrated to indicate any number of other levels of UV intensity 410 as desired, as would be apparent to persons of skill in the art. The region 225 may be any suitable shape and size as will be apparent to persons of skill in the art, and may in certain example embodiments cover all or substantially all of the upper surface 220.

The UV dosimeter 200 may be provided with a comparison chart 227, for instance on the upper surface 220, for evaluating the color, pattern, or darkness change of the UV dose indicating region 225, such as shown with respect to radiation dosimeters in U.S. Pat. No. 7,227,158 for example, which is incorporated herein by reference. For example, a comparison chart 227 may be provided with a "green" or "G" range, calibrated such that when a UV dose indicating region 225 achieves a color, pattern, or darkness indicated in the "G" range of the comparison chart 227, then a user may know that the surface 120 near where that UV dosimeter 200 was placed did receive sufficient UV intensity 410 to sufficiently sterilize that surface 120. Similarly, a comparison chart 227 may be provided with a "yellow" or "Y" range, calibrated such that when a UV dose indicating region 225 achieves a color, pattern, or darkness indicated in the "Y" range of the comparison chart 227, then a user may know that the surface 120 near where that UV dosimeter 200 was placed did NOT receive sufficient UV intensity 410 to sufficiently sterilize that surface 120, but almost received enough. Additionally, a comparison chart 227 may be provided with a "red" or "R" range, calibrated such that when a UV dose indicating region 225 achieves a color, pattern, or darkness indicated in the "R" range of the comparison chart 227, then a user may know that the surface 120 near where that UV dosimeter 200 was placed did NOT receive even close to sufficient UV intensity 410 to sterilize that surface 120. As will be apparent to persons of skill in the art, any number of ranges or gradients may be used and may be labeled in any suitable fashion. For instance, a continuously variable gradient may be provided (not shown) that varies from very light on a first end to very dark on a second end (or that fades from one color to another or one pattern to another), with a line somewhere between the ends indicating the cut-off level for minimum acceptable exposure to UV intensity 410.

Example System and Method

Figure 4:
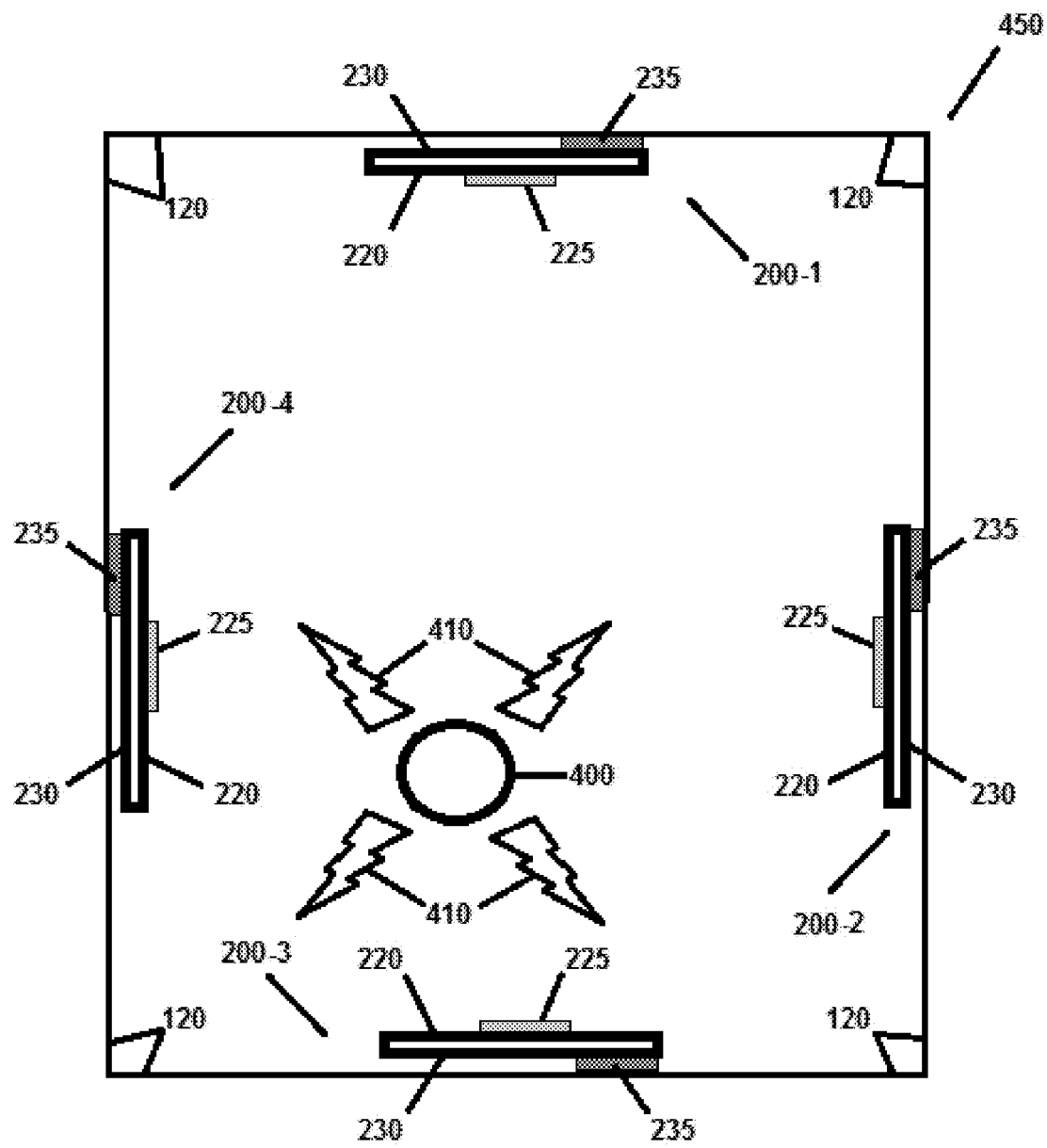
Figure 4B:
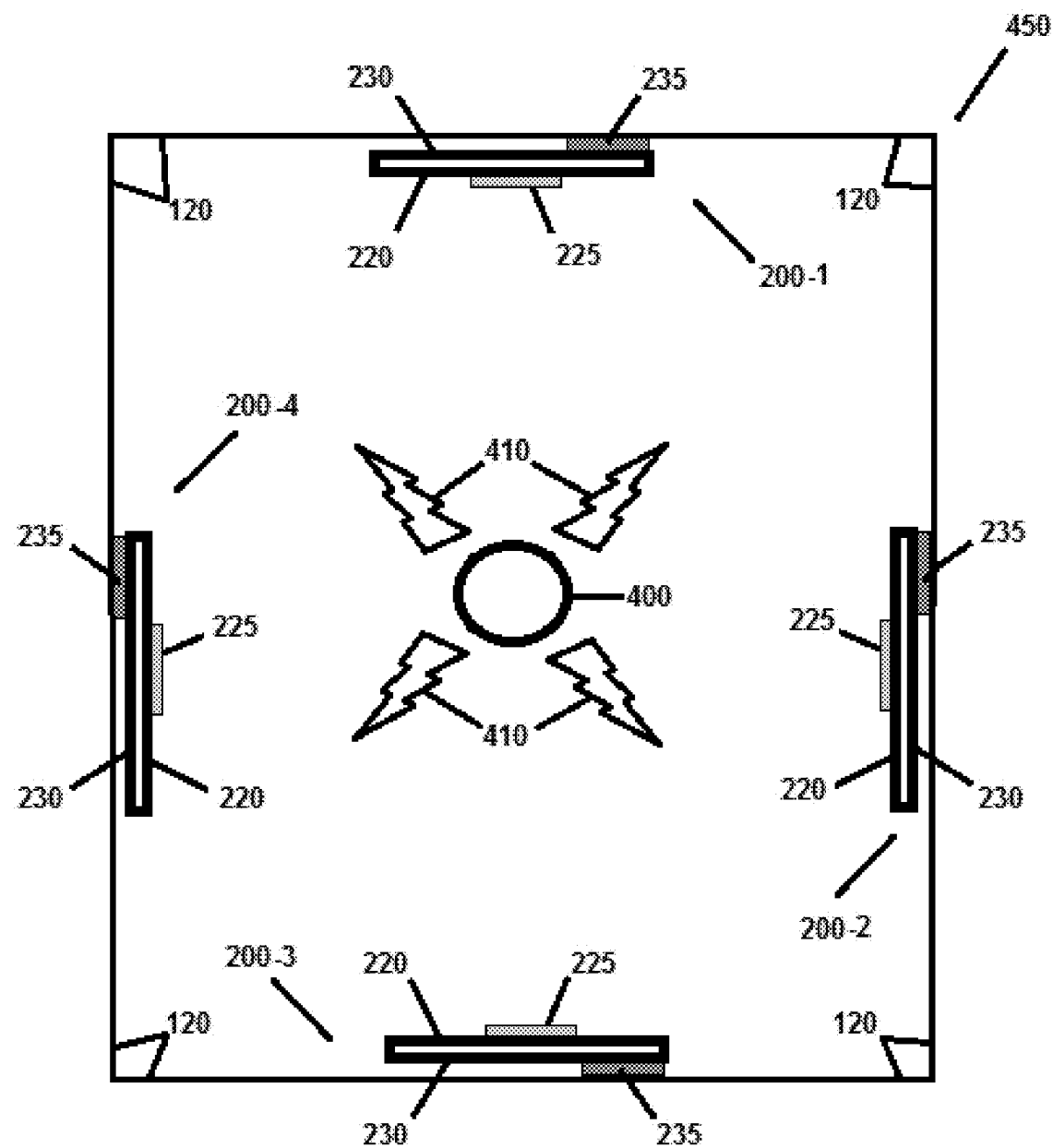

As shown in FIGS. 4A and 4B, example systems and methods may comprise, for example, removably adhering a plurality of the UV dosimeters 200-1, 200-2, 200-3, 200-4 distally around an area 450 to be disinfected by UV light 410 emanating from a UV light source 400, including in areas that appear unlikely to be in the direct line-of-sight of the UV light source 400 or that are farthest away from the UV light source 400 (e.g., UV dosimeter 200-1 in FIG. 4A), applying UV light 410 to the area 450 in a wavelength and dosage appropriate for sterilizing similar areas, for instance with one or more ultraviolet area sterilizers (UVAS) 400 (see, e.g., U.S. Pat. No. 2,215,635; U.S. Pat. No. 4,952,369; U.S. Pat. No. 4,786,812; U.S. Pat. No. 5,029,252; U.S. Pat. No. 5,446,289; U.S. Pat. No. 5,920,075; all of which are incorporated herein by reference), and then evaluating the UV dose indicating regions 225 on the UV dosimeters 200-1, 200-2, 200-3, 200-4 to determine which ones received a sufficient sterilizing dosage of UV light 410, for instance by comparing each UV dose indicating region 225 to a corresponding comparison chart 227, which may or may not be connected with or form part of the UV dosimeter 200. If any of the UV dosimeters 200-1, 200-2, 200-3, 200-4 indicate that an insufficient dosage of UV light 410 was received, it is then indicated that more UV light 410 needs to be directed to the area where that or those UV dosimeter(s) were located. Changes can then be made to the location(s) of the UVAS device(s) 400, and/or their power levels or the duration of their use, and the above steps repeated until a satisfactory result is obtained at all UV dosimeter locations. For example, in FIG. 4A the UV light source 400 is positioned furthest from UV dosimeter 200-1. In the event the configuration in FIG. 4A failed to provide enough UV light 410 to UV dosimeter 200-1, the UV light source 400 could be moved closer to UV dosimeter 200-1 as shown in FIG. 4B and the test re-run with fresh UV dosimeters.

While simple geometry for space 450 is shown in FIGS. 4A and 4B to clearly illustrate the concept of iterative configuration testing, it will be appreciated by those of skill in the art that more complex room or space geometries using one or more UV light sources 400 could present myriad potentially viable configurations for testing. But by using the present simple, inexpensive, and easy-to-use "sticky note" type UV dosimeters 200, several tests can be conducted at low cost using numerous UV dosimeters 200 all around the space 450 until a satisfactory configuration is obtained that provides sufficient UV light 410 to all surfaces 120 in the space 450.

Once a satisfactory result is obtained for all identified surfaces 120 in an area 450, the parameters and procedures of that UV treatment, including type(s) and location(s) of UV light sources 400 such as UVAS device(s), duration of their use, power level, location of furniture and other items, and any other pertinent data can be recorded, mapped, charted, or otherwise memorialized in writing and/or in a computer database or its functional equivalent so that subsequent UV sterilizations for that same area 450 can be carried out in an identical manner in the future, thereby providing assurance that subsequent UV sterilizations will sufficiently treat all surfaces 120 of that space 450, such as a hospital or clinic room or other area requiring sterilization. The following U.S. patents are incorporated herein by reference to provide additional details and options: U.S. Pat. No. 6,485,979; U.S. Pat. No. 6,656,424; U.S. Pat. No. 6,911,177; U.S. Pat. No. 8,114,342; U.S. Pat. No. 8,178,042.

In one example embodiment, provided is a method of sterilizing an area 450 such as a room until sterilized 99.99% or greater, comprising: providing a room or other area 450 that is substantially air-tight and substantially does not emit UV light 410 from inside the area 450 to outside areas where personnel may be located; providing one or more UV dosimeters 200 adapted to visually indicate when the UV dosimeters 200 have been exposed to light 410 in the UV C band range at a predetermined a fluence level, the UV dosimeters 200 being removably adhesable to surfaces 120 in the room or area 450; placing the UV dosimeters 200 in a plurality of locations in the room or area 450 and removably adhering the UV dosimeters 200 to surfaces 120 at those locations; providing one or more room sterilizer(s) 400 comprising at least one source of ultraviolet radiation or light 410 substantially in the UV C band range, locating the one or more room sterilizer(s) 400 in predetermined locations in the room or area 450; evacuating personnel (not shown) from the room or other area 450; emitting said ultraviolet light 410 from said room sterilizer(s) 400 for a predetermined time at a predetermined power level; re-entering the room or area 450 and inspecting the UV dosimeters 200; evaluating which UV dosimeters 200 indicate that they have received at least the predetermined fluence level; noting the location of any UV dosimeters 200 that did not receive at least the predetermined fluence level; determining new parameters for location(s) and/or operation of the room sterilizer(s) 400; repeating the above steps with fresh UV dosimeters 200 (that have not been exposed to the UV light 410) until all the UV dosimeters 200 indicate that they have received at least the predetermined fluence level; then recording, charting, mapping, or otherwise memorializing the procedure used that achieved at least the predetermined fluence level at all the UV dosimeters 200, including the identity(ies), orientation(s), and location(s) of the room sterilizer(s) 400, and any other pertinent parameters, such as power level, length of use, and locations of objects (not shown) in the room 450, such as furniture, electronics, medical equipment, and the like. Subsequent UV sterilizations of that particular room or area 450 or substantially similar rooms or areas 450 can then be performed by following the established procedures developed and memorialized in the foregoing steps. In certain embodiments the predetermined fluence level is at least 20 mJ/cm$^2$ of surface area. In other embodiments that predetermined fluence level may be 15, 25, 30, 35, 40, or 45 mJ/cm$^2$ of surface area, for instance. In certain example embodiments the above steps may be repeated until the room or area 450 is sterilized 99.99% or greater, or 99% or greater, or 98% or greater, for instance.

Any of the suitable technologies set forth and incorporated herein may be used to implement various example aspects of the invention as would be apparent to one of skill in the art. Although exemplary embodiments and applications of the invention have been described herein including as described above and shown in the included example Figures, there is no intention that the invention be limited to these exemplary embodiments and applications or to the manner in which the exemplary embodiments and applications operate or are described herein. Indeed, many variations and modifications to the exemplary embodiments are possible as would be apparent to a person of ordinary skill in the art. The invention may include any device, structure, method, or functionality, as long as the resulting device, system or method falls within the scope of one of the claims that are allowed by the patent office based on this or any related patent application.

What is claimed is:

1. A method of sterilizing an area, comprising the steps of:
    removably adhering two or more UV dosimeters to surfaces in a plurality of locations in an area to be sterilized, the two or more UV dosimeters adapted to visually indicate when the respective two or more UV dosimeters have been exposed to light in the UV C band range at a predetermined a fluence level, the two or more UV dosimeters being removably adhesable to each other and to surfaces in the area to be sterilized;
    positioning one or more UV sterilizers in one or more first respective locations in the area to be sterilized, the one or more UV sterilizers comprising at least one source of ultraviolet light substantially in the UV C band range;
    evacuating personnel from the area to be sterilized;
    sterilizing at least a portion of the area by causing the one or more UV sterilizers to emit ultraviolet light substantially in the UV C band range in the area to be sterilized for a predetermined first time at a predetermined first power level;
    visually inspecting the two or more UV dosimeters and evaluating whether any of the two or more UV dosimeters do not indicate exposure to light in the UV C band range at the predetermined fluence level;
    when any of the two or more UV dosimeters do not indicate exposure to light in the UV C band range at the predetermined fluence level, repeating each of the above steps using fresh UV dosimeters that have not been exposed to light in the UV C band range, while modifying the sterilizing step by positioning the one or more UV sterilizers in one or more respective locations different than the one or more respective locations used in the preceding sterilizing steps; and
    repeating each of the above steps until all of the two or more UV dosimeters used in a given sterilizing step indicate exposure to light in the UV C band range at the predetermined fluence level.

2. The method of claim 1, further comprising the steps of:
    documenting the one or more respective locations of the one or more UV sterilizers that caused all of the two or more UV dosimeters used in a given sterilizing step to indicate exposure to light in the UV C band range at the predetermined fluence level.

3. The method of claim 2, further comprising the steps of:
    sterilizing the area by positioning the one or more UV sterilizers in locations based on documentation created during the documenting step.

4. The method of claim 1, further comprising the steps of:
    identifying and documenting the location of objects in the area when all of the two or more UV dosimeters used in a given sterilizing step indicate exposure to light in the UV C band range at the predetermined fluence level, where the objects are selected from the group consisting of: furniture, electronics, medical equipment.

5. The method of claim 1, wherein the predetermined fluence level is at least 15 mJ/cm$^2$ of surface area.

6. The method of claim 1, wherein the predetermined fluence level is at least 20 mJ/cm$^2$ of surface area.

7. The method of claim 1, wherein the predetermined fluence level is at least 40 mJ/cm$^2$ of surface area.

8. A method of sterilizing an area, comprising the steps of:
    removably adhering two or more UV dosimeters to surfaces in a plurality of locations in an area to be sterilized, the two or more UV dosimeters adapted to visually indicate when the respective two or more UV dosimeters have been exposed to light in the UV C band range at a predetermined a fluence level, the two or more UV dosimeters being removably adhesable to each other and to surfaces in the area to be sterilized;
    positioning one or more UV sterilizers in one or more first respective locations in the area to be sterilized, the one or more UV sterilizers comprising at least one source of ultraviolet light substantially in the UV C band range;

evacuating personnel from the area to be sterilized;

sterilizing at least a portion of the area by causing the one or more UV sterilizers to emit ultraviolet light substantially in the UV C band range in the area to be sterilized for a predetermined first time at a predetermined first power level;

visually inspecting the two or more UV dosimeters and evaluating whether any of the two or more UV dosimeters do not indicate exposure to light in the UV C band range at the predetermined fluence level;

when any of the two or more UV dosimeters do not indicate exposure to light in the UV C band range at the predetermined fluence level, repeating each of the above steps using fresh UV dosimeters that have not been exposed to light in the UV C band range, while modifying the sterilizing step by causing the one or more UV sterilizers to emit ultraviolet light substantially in the UV C band range in the area to be sterilized for a time longer than the time in the immediately preceding sterilizing step; and repeating each of the above steps until all of the two or more UV dosimeters used in a given sterilizing step indicate exposure to light in the UV C band range at the predetermined fluence level.

9. The method of claim 8, further comprising the steps of:

documenting the length of time that the one or more UV sterilizers emitted ultraviolet light substantially in the UV C band range that caused all of the two or more UV dosimeters used in a given sterilizing step to indicate exposure to light in the UV C band range at the predetermined fluence level.

10. The method of claim 9, further comprising the steps of:

sterilizing the area by causing the one or more UV sterilizers to emit ultraviolet light substantially in the UV C band range for a length of time determined based on documentation created during the documenting step.

11. The method of claim 8, further comprising the steps of:

identifying and documenting the location of objects in the area when all of the two or more UV dosimeters used in a given sterilizing step indicate exposure to light in the UV C band range at the predetermined fluence level, where the objects are selected from the group consisting of: furniture, electronics, medical equipment.

12. The method of claim 8, wherein the predetermined fluence level is at least 15 mJ/cm$^2$ of surface area.

13. The method of claim 8, wherein the predetermined fluence level is at least 20 mJ/cm$^2$ of surface area.

14. The method of claim 8, wherein the predetermined fluence level is at least 40 mJ/cm$^2$ of surface area.

15. A method of sterilizing an area, comprising the steps of:

removably adhering two or more UV dosimeters to surfaces in a plurality of locations in an area to be sterilized, the two or more UV dosimeters adapted to visually indicate when the respective two or more UV dosimeters have been exposed to light in the UV C band range at a predetermined a fluence level, the two or more UV dosimeters being removably adhesable to each other and to surfaces in the area to be sterilized;

positioning one or more UV sterilizers in one or more first respective locations in the area to be sterilized, the one or more UV sterilizers comprising at least one source of ultraviolet light substantially in the UV C band range;

evacuating personnel from the area to be sterilized;

sterilizing at least a portion of the area by causing the one or more UV sterilizers to emit ultraviolet light substantially in the UV C band range in the area to be sterilized for a predetermined first time at a predetermined first power level;

visually inspecting the two or more UV dosimeters and evaluating whether any of the two or more UV dosimeters do not indicate exposure to light in the UV C band range at the predetermined fluence level;

when any of the two or more UV dosimeters do not indicate exposure to light in the UV C band range at the predetermined fluence level, repeating each of the above steps using fresh UV dosimeters that have not been exposed to light in the UV C band range, while modifying the sterilizing step by causing the one or more UV sterilizers to emit ultraviolet light substantially in the UV C band range in the area to be sterilized at a power level higher than the power level in the immediately preceding sterilizing step; and repeating each of the above steps until all of the two or more UV dosimeters used in a given sterilizing step indicate exposure to light in the UV C band range at the predetermined fluence level.

16. The method of claim 15, further comprising the steps of:

documenting the power level at which the one or more UV sterilizers emitted ultraviolet light substantially in the UV C band range that caused all of the two or more UV dosimeters used in a given sterilizing step to indicate exposure to light in the UV C band range at the predetermined fluence level.

17. The method of claim 16, further comprising the steps of:

sterilizing the area by causing the one or more UV sterilizers to emit ultraviolet light substantially in the UV C band range at a power level determined based on documentation created during the documenting step.

18. The method of claim 15, further comprising the steps of:

identifying and documenting the location of objects in the area when all of the two or more UV dosimeters used in a given sterilizing step indicate exposure to light in the UV C band range at the predetermined fluence level, where the objects are selected from the group consisting of: furniture, electronics, medical equipment.

19. The method of claim 15, wherein the predetermined fluence level is at least 15 mJ/cm$^2$ of surface area.

20. The method of claim 15, wherein the predetermined fluence level is at least 20 mJ/cm$^2$ of surface area.

* * * * *